(12) United States Patent
Giurgiutiu et al.

(10) Patent No.: US 7,881,881 B2
(45) Date of Patent: Feb. 1, 2011

(54) STRUCTURAL HEALTH MONITORING APPARATUS AND METHODOLOGY

(75) Inventors: Victor Giurgiutiu, Columbia, SC (US); Lingyu Yu, Columbia, SC (US); Giola Santoni Bottai, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 12/539,986

(22) Filed: Aug. 12, 2009

(65) Prior Publication Data

US 2010/0042338 A1 Feb. 18, 2010

Related U.S. Application Data

(60) Provisional application No. 61/088,047, filed on Aug. 12, 2008.

(51) Int. Cl.
*G06F 19/00* (2006.01)
(52) U.S. Cl. ........................................................ 702/39
(58) Field of Classification Search ................... 702/39
See application file for complete search history.

(56) References Cited

U.S. PATENT DOCUMENTS

| | | | |
|---|---|---|---|
| 2,440,198 A | 4/1948 | Green | |
| 3,713,127 A | 1/1973 | Keledy et al. | |
| 4,821,575 A | 4/1989 | Fujikake et al. | |
| 4,995,260 A | 2/1991 | Deason et al. | |
| 5,167,157 A | 12/1992 | Wertz et al. | |
| 5,814,729 A | 9/1998 | Wu et al. | |
| 6,006,163 A | 12/1999 | Lichtenwalner et al. | |
| 6,768,312 B2 | 7/2004 | Sun et al. | |
| 6,996,480 B2 | 2/2006 | Giurgiutiu et al. | |
| 7,024,315 B2 | 4/2006 | Giurgiutiu | |
| 7,034,660 B2 | 4/2006 | Watters et al. | |
| 2008/0288184 A1 | 11/2008 | Giurgiutiu et al. | |
| 2010/0132469 A1* | 6/2010 | Giurgiutiu et al. | ............ 73/628 |

OTHER PUBLICATIONS

Giurgiutiu, et al., *Development of a Field-Portable Small-Size Impedance Analyzer for Structural Health Monitoring using the Electromechanical Impedance Technique*, SPIE's 11th Annual International Symposium on Smart Structures and Materials and 9th Annual International Symposium on NDE for Health Monitoring and Diagnostics, Mar. 14-18, 2004, San Diego, CA, paper #5391-92, (12 pages).

(Continued)

*Primary Examiner*—Tung S Lau
(74) *Attorney, Agent, or Firm*—Dority & Manning, P.A.

(57) ABSTRACT

Disclosed is an apparatus and methodology for structural health monitoring (SHM) in which smart devices interrogate structural components to predict failure, expedite needed repairs, and thus increase the useful life of those components. Piezoelectric wafer active sensors (PWAS) are applied to or integrated with structural components and various data collected there from provide the ability to detect and locate cracking, corrosion, and disbanding through use of pitch-catch, pulse-echo, electro/mechanical impedance, and phased array technology. Stand alone hardware and an associated software program are provided that allow selection of multiple types of SHM investigations as well as multiple types of data analysis to perform a wholesome investigation of a structure.

18 Claims, 4 Drawing Sheets

OTHER PUBLICATIONS

Peairs, D.M.; Park, G.; Inman, D.J. "Low Cost Impedance Monitoring Using Smart Materials", Proceeding of the First European Workshop on Structural Health Monitoring, Ecole Normale Superieure, Cachan (Paris), France, Jul. 10-12, 2002.

Peairs, D.M.; Park, G.; Inman, D.J. "Improving Accessibility of the Impedance-Based Structural Health Monitoring Method", Journal of Intelligent Materials Systems and Structures, vol. 15, 129-139, Feb. 2004.

Application No. 041, "The Fundamentals of FFT-Based Signal Analysis and Measurement in LabVIEW and LabWindows", NI, Nov. 1993.

Searle, A.; Kirkup, L., "Real time impedance plots with arbitrary frequency components", Physiological Measurement, vol. 20, 103-114, Feb. 1999.

Darowicki, K.; et al., "Continuous-frequency Method of Measurement of Electrode Impedance", Instrumentation Science & Technology, vol. 31, No. 1, pp. 53-62, 2003.

* cited by examiner

STRUCTURAL HEALTH MONITORING APPARATUS AND METHODOLOGY

CROSS-REFERENCE TO RELATED APPLICATION

The present application is based on and claims priority to U.S. Provisional Application 61/088,047 having a filing date of Aug. 12, 2008, which is incorporated by reference herein.

GOVERNMENT SUPPORT CLAUSE

The present invention was developed with funding from NASA-STTR Grant number NGAI 05.0068. Therefore, the government retains certain rights in this invention.

FIELD OF THE INVENTION

The present subject matter relates to apparatus and methodologies for monitoring structural integrity. More specifically, the present subject matter relates to apparatus and methodologies employing ultrasonic devices and associated analysis software to perform investigations of a structure.

BACKGROUND OF THE INVENTION

Structural health monitoring (SHM) is a method of determining the health of a structure from the readings of an array of permanently-attached sensors that are embedded into the structure and monitored over time. SHM can be performed in two basic ways, passively and actively. Passive SHM corresponds to monitoring a number of structure related parameters including, but not limited to, loading stress, environment action, performance indicators, acoustic emission from cracks, and inferring the state of structural health from a structural model. In contrast, active SHM performs proactive interrogation of the structure, detects damage, and determines the state of structural health from the evaluation of damage extend and intensity. Both approaches aim at performing a diagnosis or analysis of the structural safety and health, to be followed by a prognosis of the remaining life. Passive SHM uses passive sensors which only "listen" but do not interact with the structure. Therefore, they do not provide direct measurement of the damage presence and intensity. Active SHM uses active sensors that interact with the structure and thus determine the presence or absence of damage. The methods used for active SHM resemble those of nondestructive evaluation (NDE), e.g., ultrasonics, eddy currents, etc., only that they are used with embedded sensors. Hence, active SHM could be seen as a method of embedded NDE. One widely used active SHM method employs piezoelectric wafer active sensors as described, for example, in U.S. Pat. No. 7,024,315, which discloses sending and receiving Lamb waves to determine the presence of cracks, delamination, de-bonding, and corrosion. Due to its similarities to NDE ultrasonics, this approach is also known as embedded ultrasonics.

In order to thoroughly investigate the state of health of structural components, different methods are needed. Impedance is useful to detect corrosion, pitch-catch and pulse-echo are used to detect through the thickness damage, and phase-array is used for non-destructive evaluation methods (NDE). After data collection is performed, the data must be analyzed. Each method requires a different approach for data analysis. Different hardware and software are available for data processing, but often the data must be manually transformed to be used in the software. In order to make the SHM process smoother and quicker, both integrated hardware components and integrated software to collect, process, and display the results are needed.

A structural component can deteriorate or brake for different reasons. Corrosion on metallic structures reduces the thickness of the component and hence its ability to sustain load. If the thickness goes below a critical value, the structure is no longer able to resist the design load and will eventually brake. Cracks in metallic structure can lead to catastrophic failures due to either fatigue load or static load. Composite structures can fail because of delamination, de-bonding, or because of impact damages. The SHM operator must use different kinds of methods to determine whether a structure is healthy or not.

Wave propagation is often used for crack and delamination, but different damage locations in the thickness of the structure requires different wave modes. Electromechanical (E/M) methodologies may be used for corrosion detection and to test the integrity of the sensor-to-structure bonding. Each method requires a different hardware component with a corresponding dedicated software component. After data collection is performed the operator must format the collected data to the specific data analysis software to derive conclusions on the health of the structure. The entire process can be confusing and can easily lead to errors and missing data. Moreover it is time consuming and memory consuming because the data are often duplicated to adapt to the format of the data analysis software.

In order to develop any of the SHM technique several sensors are needed. During data collection several piezoelectric wafer active sensors (PWAS) may be interrogated at the same time. Automatic data collection systems that permit an operator to perform data acquisition from the all desired sensors by pressing one button are known. In addition, phase-array data processing systems are known that perform NDE through virtual beam forming. U.S. Pat. No. 6,996,480 B2 illustrates such a system. For the latter method, different PWAS array configurations are needed. The increasing number of PWAS for phase-array method means an increasing number of wiring and electronic cross-talking.

While various implementations of structural health monitoring devices and have been developed, and while various methodologies have been proposed to evaluate structural health, no design has emerged that generally encompasses all of the desired characteristics as hereafter presented in accordance with the subject technology.

SUMMARY OF THE INVENTION

In view of the recognized features encountered in the prior art and addressed by the present subject matter, improved apparatus and methodologies for implementing structural health monitoring (SHM) have been provided.

In an exemplary configuration, software is provided for automatic control of associated hardware for providing user selectable operational environments for structural health monitoring.

In one of its simpler forms, an integrated software program has been developed to permit simplified selection of various structural health monitoring aspects including ability to detect and locate cracking, corrosion, and disbanding through use of pitch-catch, pulse-echo, electro/mechanical impedance, and phased array technology.

Another positive aspect of this type of device is that stand alone hardware and an associated single software package has been provided that permits performance of all needed SHM investigations to assess the health of a structure.

In accordance with aspects of certain embodiments of the present subject matter, methodologies are provided to selective evaluate collected structural health data using manually selectable multiple methodologies.

In accordance with certain aspects of other embodiments of the present subject matter, methodologies have been developed to analyze collected data using root mean square deviation to produce scalar numbers representing relationships between compared data points.

In accordance with yet additional aspects of further embodiments of the present subject matter, apparatus and accompanying methodologies have been developed to permit direct calculation of a damage index.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the invention without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Repeat use of reference characters throughout the present specification and appended drawings is intended to represent same or analogous features or elements of the invention.

DETAILED DESCRIPTION OF THE PREFERRED EMBODIMENTS

As discussed in the Summary of the Invention section, the present subject matter is particularly concerned with methods and apparatus for use in conjunction with structural health monitoring and evaluation.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

Reference will now be made in detail to the presently preferred embodiments of the subject structural health monitoring apparatus and methodology. For a thorough structural health monitoring (SHM) investigation, several hardware components are needed including a function generator, an oscilloscope, an impedance analyzer, and an automatic signal collection unit. Most of these components are available commercially and it is possible to acquire small components directly such that it is possible to integrate all the components as a small, compact device. The automatic signal collection unit has been described in Publication No. WO/2006/017795 corresponding to International Application No. PCT/US2005/028016 published on Feb. 16, 2006 entitled "AUTOMATIC SIGNAL COLLECTION AND ANALYSIS FOR PIEZOELECTRIC WAFER ACTIVE SENSOR" and corresponding to U.S. patent application Ser. No. 11/659,071 filed Jan. 31, 2007 which is incorporated herein for all purposes.

Figure 1:
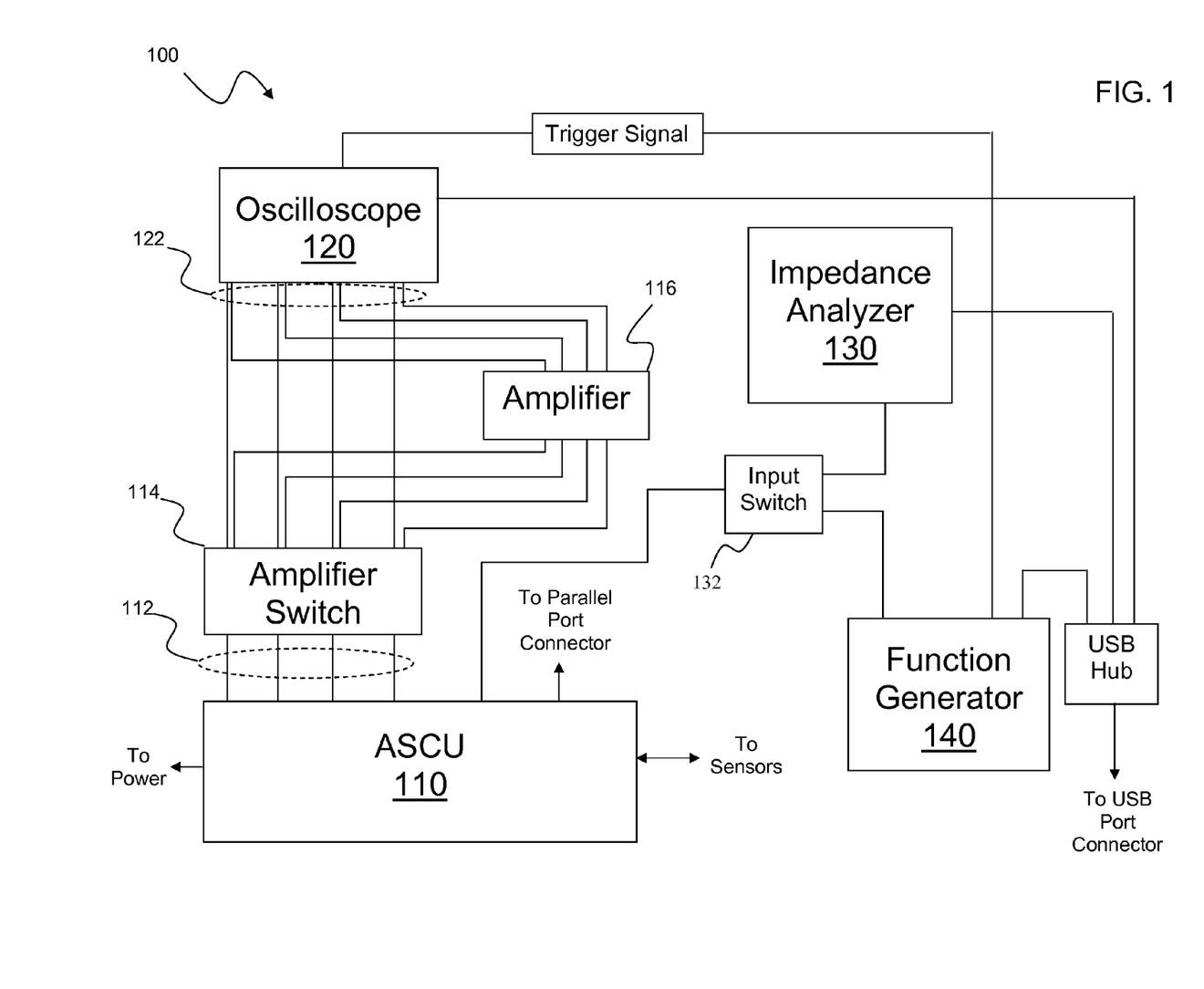
FIG. 1 schematically illustrates an exemplary hardware configuration usable in combination with operational software for implementing the present subject matter.

Referring now to the drawings, FIG. 1 illustrates exemplary hardware 100 that may be used in combination with operational software to be described later, for implementing the present subject matter. As illustrated in FIG. 1, the hardware component of the present subject matter generally corresponds to an automatic signal collection unit (ASCU) 110 which may receive signals from a number of sensors, as will be described more fully later with respect to FIG. 3. These signals are collected as data by ASCU 110 and sent over output lines 112 to oscilloscope 120 for display thereon. An amplifier 116 may be selectively inserted in the lines 112 by way of amplifier switch 114 prior to application to input lines 122 of oscilloscope 120. In an exemplary configuration, amplifier 116 may be directly integrated on ASCU 110 while a switch (not illustrated) may be used to bypass the amplifier.

Switch 132 may be used to activate the impedance analyzer 130 or the function generator 140. The various hardware components can be connected to a computer through a USB port as described later with respect to FIG. 3. Oscilloscope 120 and function generator 140 are connected through a parallel port for triggering of the signal. In exemplary configurations, ASCU 110 may be connected to the sensors through a cable or they may be connected wireless to ASCU 110. To perform structural health monitoring (SHM) with the hardware described above, the following software program modules, which may be combined into a single software program, may be provided: pitch-catch data collection, pulse-echo data collection, round-robin data collection, impedance data collection, DI analyzer for pitch-catch and pulse-echo data, DI analyzer for impedance data, embedded ultrasonics structural radar (EUSR) for phase-array (round robin) data, and capacitance measurement.

Depending on the particular software implementation, in exemplary embodiments of the present subject matter, an initial window may be displayed to illustrate possible selection types with a subsequent window opened showing the selected data collection type. Those of ordinary skill in the art will appreciate that further windows illustrating various selection options as well as other displays including, but not limited to, output displays may be provided again depending on the particular software implementation selected. The remainder of the description of the various exemplary embodiments of the present subject matter will be discussed under the assumption that various windows providing selection and other options are employed. In an exemplary embodiment, software usable with the present subject matter may be developed using LabVIEW®, however such is not a limitation of the present subject matter as fully functional software may be implemented by those of ordinary skill in the art using any suitable programming language.

Figure 2:
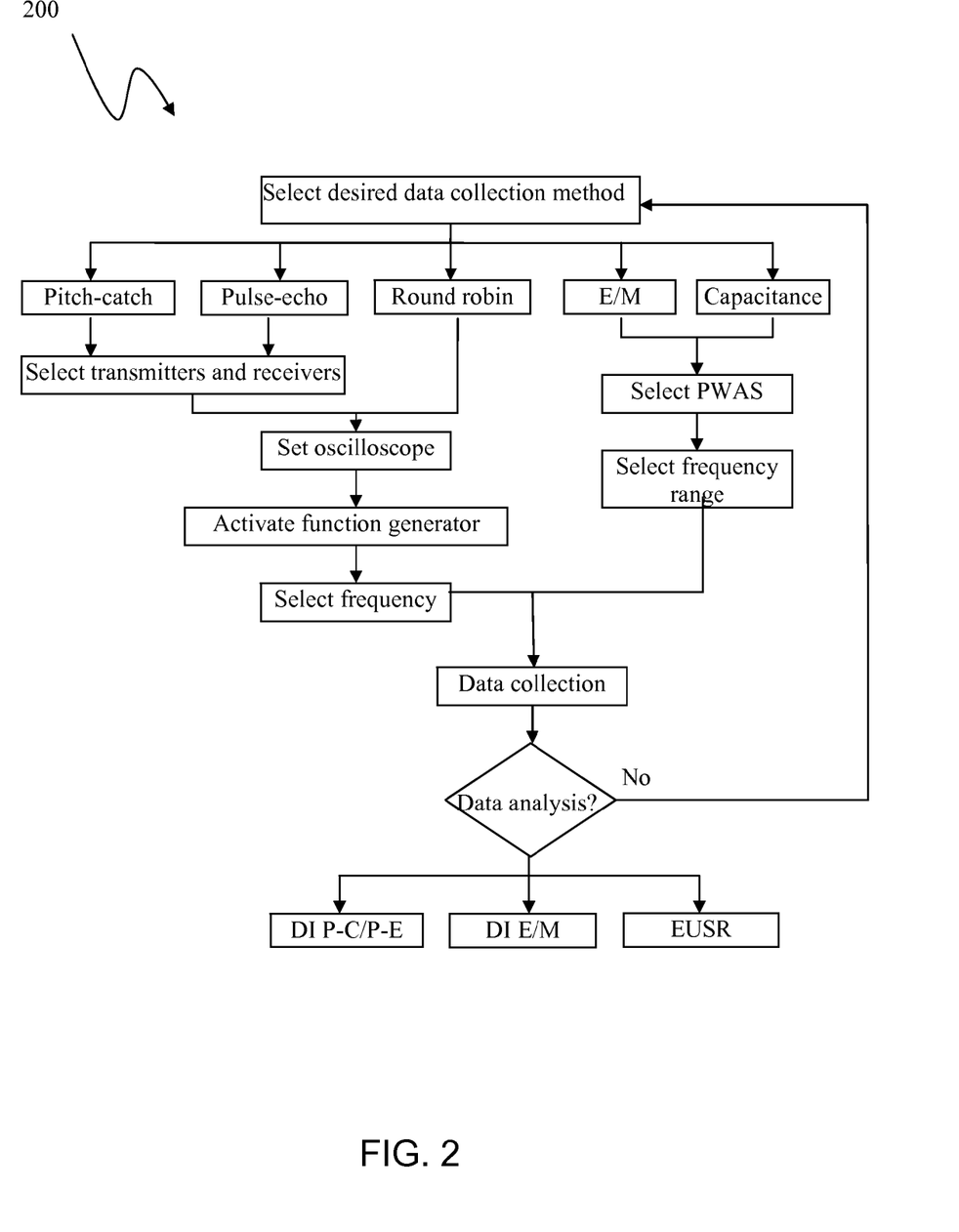
FIG. 2 is a flow chart representation of exemplary software usable with the hardware illustrated in FIG. 1 to implement the present subject matter.

The interface program is divided into five different environments. The first three, Pitch Catch, Phase Array, and Impedance, are for data collection while the second two are for data analysis. An initial window may be provided illustrating each of these environments using, for example, a push button type display where a user may make a selection using, for example, a mouse type pointing device. It is also possible to possible to stop the Shell program through a similarly displayed Stop button. Run and Pause buttons may also be provided. A self-explanatory flow chart 200 is presented in FIG. 2 showing the general steps involved in the various selectable environments as described herein after.

By pressing the Pitch Catch button, a pitch-catch/pulse-echo environment window opens. This window may be configured to display several Tabs offering additional options.

In data collection windows, options are provided to select which transducers the user wants to use. It is possible to perform data analysis right after data collection or to continue with data collection with another method or the same as before. All the data and results are saved in a folder specified by the user with the name specified by the user.

The first tab of the Pitch Catch environment is a SETUP tab. The set up for this window depends on the kind of specimen and frequency you are using. The tabs that need to be checked and eventually to be changed before doing data collection are: Post Sample; Trigger value; Sample Frequency. Knowing the frequency and the speed of the excited wave, it is possible to select the sample frequency such as to be able to record the desired wave.

A second tab in the Pitch Catch environment is a Control Panel tab. By selecting this tab, it is possible to select transmitter sensors and receiver sensors. It is possible to load an external file were a recorded interrogation sequence or it is possible to add the sequence manually. Other options are: selection of folder where the data will be saved and specify the name of the sub folder in a Name tab. The user can set the number of average to compute before saving the data collected.

Within the Pitch Catch environment, data collection progress may be visualized by selecting a third tab, a Display Panel tab. The Display Panel may show a number of different graphical displays displaying waveform graphs illustrating, for example, signal amplitude vs. time. When data collection is finished, the program will return to the initial window of the shell program.

From the initial window of the shell program, a Round Robin environment may be selected by pressing a Round Robin button where upon a phase array environment opens. Here again, a number of different option tabs may be presented including, for example, SETUP, Control Panel, and Display Panel options. The setup window is the same or similar to that for the Pitch Catch environment. For data processing with the EUSR program, the user should check that post-sample is set to 1. To perform round robin data collection, the user must enter the total number of sensors connected or the last number of the wiring connection. Each of the sensors provided in the configuration may be associated with an indicator light/control on the setup window. If the user does not want to take data from some of the sensors connected, it is possible to deselect them by turning off the indicator light associated with the corresponding sensor. When the program has finished collecting data, it will close the Phase Array window and return to the initial Shell window. The Display Panel window is the same or similar to that for the Pitch Catch environment.

From the initial window of the shell program, an Impedance environment may be selected by pressing an Impedance button where upon an impedance environment window opens. In this environment window, the user can specify the total number of sensors available and select or deselect the sensors the user wants to interrogate. It is possible to specify also the total number of points to record in a selected frequency range. Selecting the Start button the program will display the real and imaginary impedance graphs, store the data, and display the PWAS capacitance. After the program has finished it will return to the initial shell window.

As previously noted, the initial shell window provides two options for data analysis, Damage Index (DI) for Pitch Catch and Damage Index for Impedance. The DI software is used to assess the severity of the damage in a structure. The damage metric is a scalar quantity that results from the comparative processing of the signal under consideration. The damage metric should reveal the difference between readings (impedance spectrum or wave packets) due to the presence of damage. Ideally the damage index would be a metric which captures only the spectral features that are directly modified by the damage presence, while neglecting the variations due to normal operation conditions (i.e., statistical difference within a population of specimens, and expected changes in temperature, pressure, ambient vibrations, etc.). Several damage metrics may be used to compare impedance spectra or wave packages and assess the presence of damage. In this program, root mean square deviation (RMSD) is used and the mathematical expressions, given in terms of the signal, is as follows:

$$RMSD = \sqrt{\frac{\sum_N [\text{Re}(S_i) - \text{Re}(S_i^0)]^2}{\sum_N [\text{Re}(S_i^0)]^2}}$$

where, the superscript 0 signifies the pristine state of the structure and N is the number of data points. This equation yields a scalar number, which represents the relationship between the compared readings. The advantage is that the data do not need any preprocessing, i.e., the data obtained from the measurement equipment can be directly used to calculate the damage index.

Figure 3:
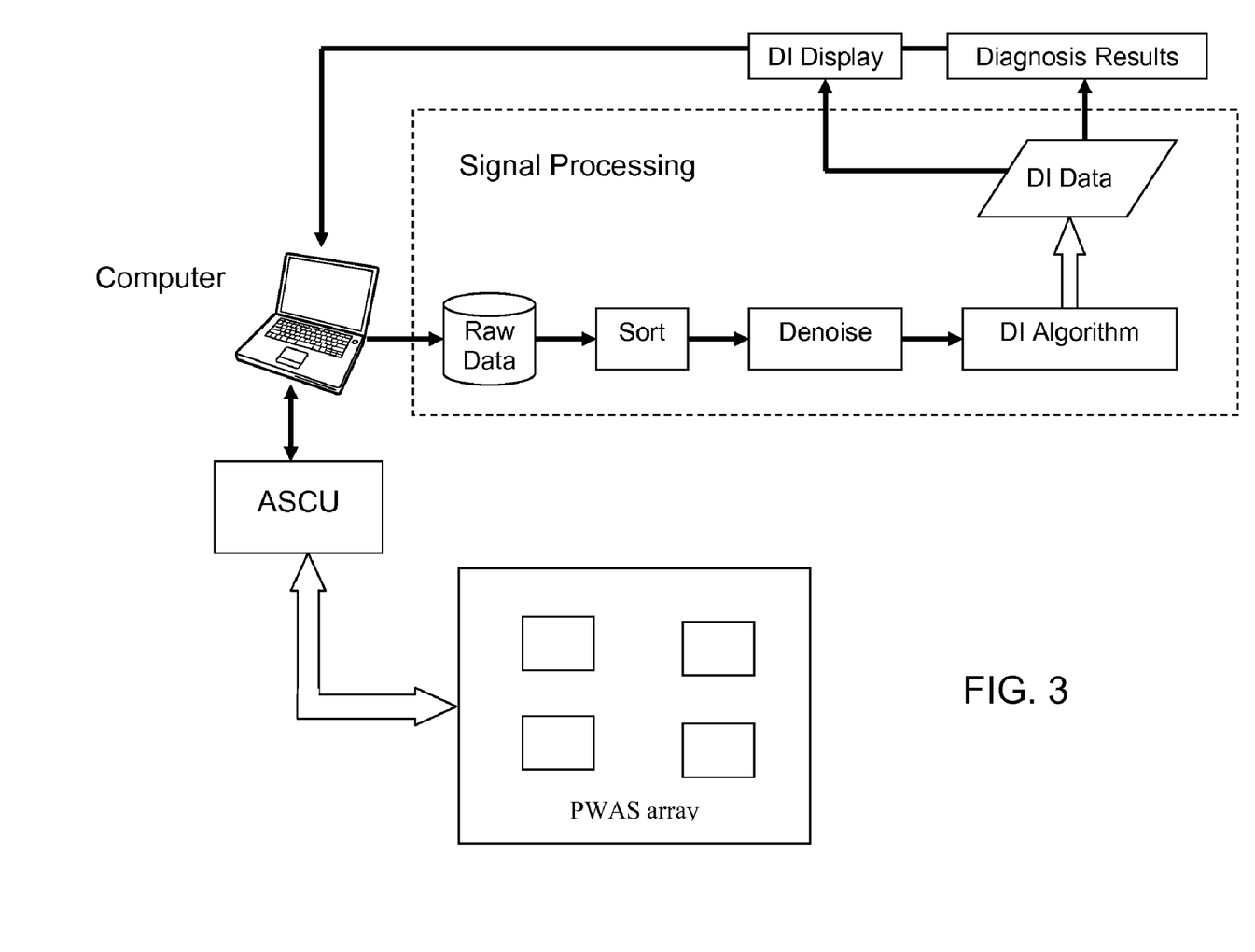
FIG. 3 is a flow chart representation of an exemplary damage index diagnosis signal processing methodology in accordance with the present subject matter.

With reference to FIG. 3, there is illustrated a flow chart representation of an exemplary damage index diagnosis signal processing methodology in accordance with the present subject matter. Signals from a PWAS array are collected by way of an oscilloscope associated with an automatic signal collection unit (ASCU) and the data are recorded on a computer.

Figure 4:
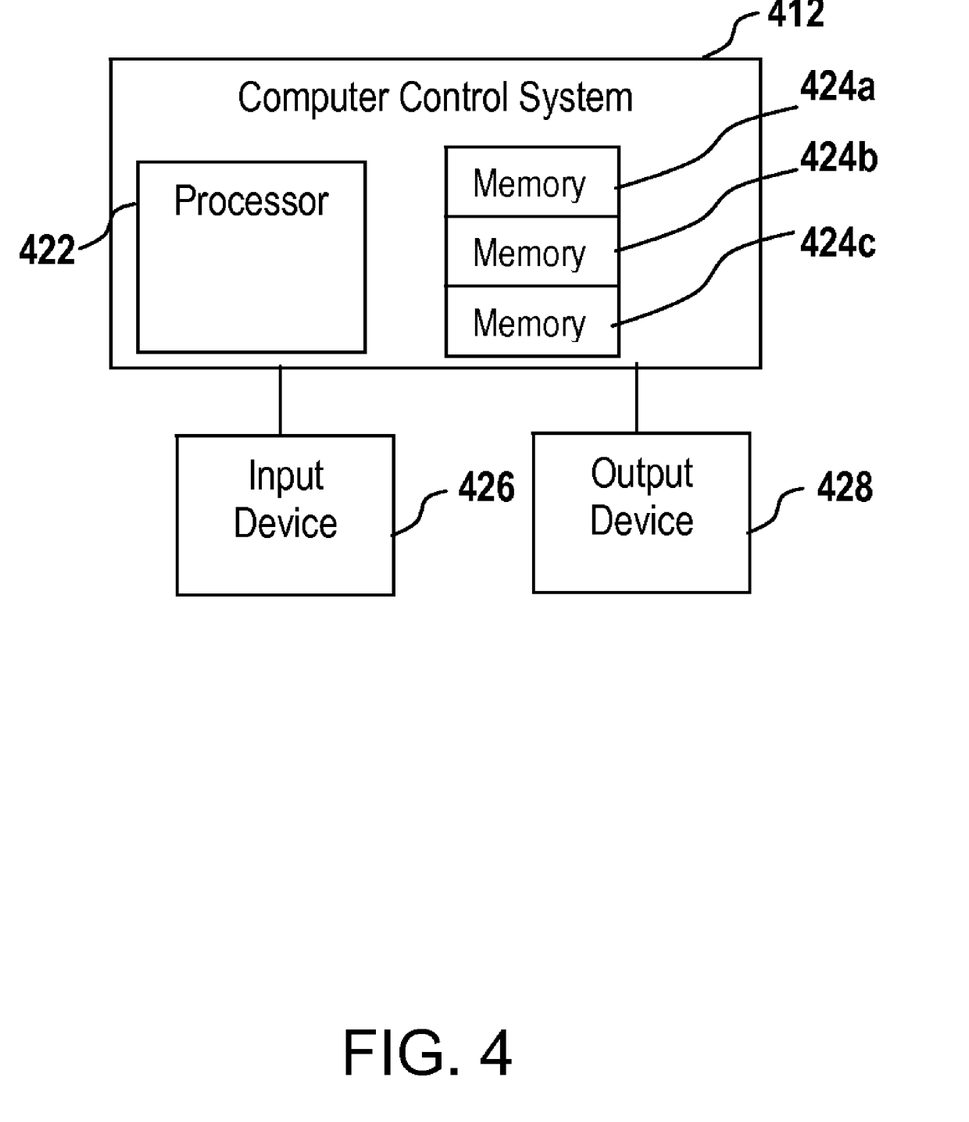
FIG. 4 illustrates a computer in accordance with the present subject matter.

Computer 412 may generally include such components as at least one memory/media element or database for storing data and software instructions as well as at least one processor. In the particular example of FIG. 4, a processor(s) 422 and associated memory/media elements 424a, 424b and 424c are configured to perform a variety of computer-implemented functions (i.e., software-based data services). At least one memory/media element (e.g., element 424b in FIG. 4) is dedicated to storing software and/or firmware in the form of computer-readable and executable instructions that will be implemented by the one or more processor(s) 422. Other memory/media elements (e.g., memory/media elements 424a, 424c) are used to store data which will also be accessible by the processor(s) 422 and which will be acted on per the software instructions stored in memory/media element 424b. The various memory/media elements of FIG. 4 may be provided as a single or multiple portions of one or more varieties of computer-readable media, such as but not limited to any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others. Although FIG. 4 shows three separate memory/media elements 424a, 424b and 424c, the content dedicated to such devices may actually be stored in one memory/media element or in multiple elements, Any such possible variations and other variations of data storage will be appreciated by one of ordinary skill in the art.

In one particular embodiment of the present subject matter, a first portion of memory/media 424a is configured to store input data for the subject structural health monitoring system. Input data stored in memory/media element 424a may include raw measurement data exported from the ASCU from the PWAS array. Data in memory 424a may also include input parameters provided from a user. Although such user-established limits and other input data may be pre-programmed into memory/media element 424a, they may also be entered as input data from a user accessing an input device 426, which may correspond to one or more peripheral devices configured to operate as a user interface with computer 412. Exemplary input devices may include but are not limited to a keyboard, touch-screen monitor, microphone, mouse and the like.

Second memory element 424b includes computer-executable software instructions that can be read and executed by processor(s) 422 to act on the data stored in memory/media element 424a to create new output data (e.g., Damage Index data) for storage in a third memory/media element 424c. Such output data may be provided to a peripheral output device 428, such as monitor, printer or other device for visually depicting the output data, or as control signals to still further components. Computing/processing device(s) 422 may be adapted to operate as a special-purpose machine by executing the software instructions rendered in a computer-readable form stored in memory/media element 424b. When software is used, any suitable programming, scripting, or other type of language or combinations of languages may be used to implement the teachings contained herein. In other embodiments, the methods disclosed herein may alternatively be implemented by hard-wired logic or other circuitry, including, but not limited to application-specific circuits.

The program will automatically read all history data for all sensors in the network at various frequency and process with DI algorithm. Denoising is by default in the pre-processing part, but it can be deselected if needed. After that, the DI algorithm will analyze all history data for all PWAS pairs and generate a DI data file stored in the same folder. The program will also provide a diagnosis finding out which PWAS pair is suffering the maximum change (as damaged) and which one is suffering the minimum change (as undamaged). The user can also choose to observe, by way of a DI Display Panel, the DI curve for any single PWAS or PWAS pair in the program.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A system for structural health monitoring comprising:
an automatic signal collection unit;
an array of sensors;
an oscilloscope;
a function generator;
an impedance analyzer; and
a computer, wherein the computer is programmed to perform structural health monitoring analysis based on user selectable data wherein the structural health monitoring analysis programming utilizes $$RMSD = \sqrt{\frac{\sum_N [Re(S_i) - Re(S_i^0)]^2}{\sum_N [Re(S_i^0)]^2}}$$

to perform a damage index analysis.

2. A system as in claim 1, wherein the user selectable data comprises pitch-catch data.

3. A system as in claim 1, wherein the user selectable data comprises pulse-echo data.

4. A system as in claim 1, wherein the user selectable data comprises round-robin data.

5. A system as in claim 1, wherein the user selectable data comprises impedance data.

6. A system as in claim 1, wherein the user selectable data comprises capacitance data.

7. A system as in claim 1, wherein the structural health monitoring analysis comprises embedded ultrasonics structural radar for phase-array data.

8. A system as in claim 1, wherein the structural health monitoring analysis comprises a damage index analysis for pitch-catch and pulse-echo data.

9. A system as in claim 1, wherein the structural health monitoring analysis comprises a damage index analysis for impedance data.

10. A system as in claim 1, wherein the array of sensors comprises piezoelectric wafer active sensors.

11. A system as in claim 1, further comprising an amplifier for selectively amplifying signals produced by the sensors.

12. A system as in claim 1, further comprising a switch to activate the impedance analyzer or function generator.

13. A system as in claim 10, wherein the sensors are wireless sensors.

14. A method for structural health monitoring comprising:
utilizing a system to perform structural health monitoring analysis based on user selectable data, the system comprising an automatic signal collection unit, an array of sensors, an oscilloscope, a function generator, an impedance analyzer, and a computer; wherein the computer performs structural health monitoring analysis based on data that is selected wherein the structural health monitoring analysis utilizes $$RMSD = \sqrt{\frac{\sum_N [Re(S_i) - Re(S_i^0)]^2}{\sum_N [Re(S_i^0)]^2}}$$

to perform a damage index analysis.

15. A method as in claim 14, wherein the data that is selected comprises pitch-catch data.

16. A system as in claim 14, wherein the data that is selected comprises pulse-echo data.

17. A system as in claim 14, wherein the data that is selected comprises round-robin data.

18. A system as in claim 14, wherein the data that is selected comprises impedance data.

* * * * *

UNITED STATES PATENT AND TRADEMARK OFFICE
CERTIFICATE OF CORRECTION

| | | |
|---|---|---|
| PATENT NO. | : 7,881,881 B2 | Page 1 of 1 |
| APPLICATION NO. | : 12/539986 | |
| DATED | : February 1, 2011 | |
| INVENTOR(S) | : Giurgiutiu et al. | |

It is certified that error appears in the above-identified patent and that said Letters Patent is hereby corrected as shown below:

On the Title page, line 8 under Section (57) Abstract, please delete the word "disbanding" and insert the word --disbonding--.

Signed and Sealed this
Nineteenth Day of July, 2011

David J. Kappos
*Director of the United States Patent and Trademark Office*